(12) United States Patent
Covach et al.

(10) Patent No.: US 11,389,163 B2
(45) Date of Patent: Jul. 19, 2022

(54) SURGICAL STAPLER WITH EXPANDABLE JAW

(71) Applicant: Applied Medical Resources Corporation, Rancho Santa Margarita, CA (US)

(72) Inventors: Jonathan Covach, Mission Viejo, CA (US); Matthew M. Becerra, Lake Forest, CA (US); Gary M. Johnson, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 17/024,367

(22) Filed: Sep. 17, 2020

(65) Prior Publication Data

US 2021/0000468 A1  Jan. 7, 2021

Related U.S. Application Data

(63) Continuation of application No. 15/788,118, filed on Oct. 19, 2017, now Pat. No. 10,888,326, which is a
(Continued)

(51) Int. Cl.
*A61B 17/072* (2006.01)
*A61B 17/00* (2006.01)

(52) U.S. Cl.
CPC .......... *A61B 17/07207* (2013.01); *A61B 2017/0046* (2013.01); *A61B 2017/00477* (2013.01); *A61B 2017/07257* (2013.01)

(58) Field of Classification Search
CPC ........ A61B 17/07207; A61B 17/07257; A61B 17/00477; A61B 17/0046
See application file for complete search history.

(56) References Cited

U.S. PATENT DOCUMENTS 2,073,960 A  3/1937  Crosby
2,140,593 A  12/1938 Pankonin
(Continued)

FOREIGN PATENT DOCUMENTS

EP  0 251 444 A1  1/1988
EP  0 492 283 A1  7/1992
(Continued)

OTHER PUBLICATIONS

European Patent Office, Extended European Search Report for European Application No. EP 20197859.0, entitled "Surgical Stapler with Circumferential Firing," dated Jan. 28, 2021, 13 pgs.
(Continued)

*Primary Examiner* — Thomas M Wittenschlaeger
(74) *Attorney, Agent, or Firm* — John F. Heal

(57) ABSTRACT

Jaw assemblies for a surgical stapler are provided. The jaw assemblies comprise a first jaw having a first clamping surface and a plurality of staples disposed therein and second jaw assembly having a second clamping surface. The jaw assemblies can be actuated from a closed configuration in which the first clamping surface contacts or is adjacent to the second clamping surface to an open configuration in which the second jaw is pivoted away from the first jaw to a stapling position in which the second clamping surface is parallel to the first clamping surface and spaced apart from the first clamping surface. A pivoting link or sliding pivot joint can couple the second jaw to the first jaw to facilitate motion between the closed position, the open position, and the stapling position.

20 Claims, 12 Drawing Sheets

Related U.S. Application Data continuation of application No. 14/211,570, filed on Mar. 14, 2014, now Pat. No. 9,820,742.

(60) Provisional application No. 61/793,065, filed on Mar. 15, 2013.

(56) References Cited

U.S. PATENT DOCUMENTS

| | | | |
|---|---|---|---|
| 2,351,608 A | 6/1944 | Greenwood | |
| 2,487,565 A | 11/1949 | Leber et al. | |
| 2,641,154 A | 6/1953 | Heller | |
| 3,076,373 A | 2/1963 | Matthews | |
| 3,077,812 A | 2/1963 | Dietrich | |
| 3,080,564 A | 3/1963 | Strekopitov et al. | |
| 3,203,220 A | 8/1965 | Kaepernik | |
| 3,252,643 A | 5/1966 | Strekopitov et al. | |
| 3,273,562 A | 9/1966 | Brown | |
| 3,373,646 A | 3/1968 | Ehlert | |
| 3,459,187 A | 8/1969 | Pallotta | |
| 3,494,533 A * | 2/1970 | Green | A61B 17/072 227/19 |
| 3,662,939 A | 5/1972 | Bryan | |
| 3,675,688 A | 7/1972 | Bryan et al. | |
| 3,692,224 A | 9/1972 | Astafiev et al. | |
| 4,261,244 A | 4/1981 | Becht et al. | |
| 4,281,785 A | 8/1981 | Brooks | |
| 4,304,236 A | 12/1981 | Conta et al. | |
| 4,312,363 A | 1/1982 | Rothfuss et al. | |
| 4,317,451 A | 3/1982 | Cerwin et al. | |
| 4,407,286 A | 10/1983 | Noiles et al. | |
| 4,434,796 A | 3/1984 | Karapetian et al. | |
| 4,442,964 A | 4/1984 | Becht | |
| 4,454,875 A | 6/1984 | Pratt et al. | |
| 4,522,327 A | 6/1985 | Korthoff et al. | |
| 4,527,724 A | 7/1985 | Chow et al. | |
| 4,589,582 A | 5/1986 | Bilotti | |
| 4,591,085 A | 5/1986 | Di Giovanni | |
| 4,606,344 A | 8/1986 | Di Giovanni | |
| 4,608,981 A * | 9/1986 | Rothfuss | A61B 17/07207 227/180.1 |
| 4,728,020 A | 3/1988 | Green et al. | |
| 4,805,823 A | 2/1989 | Rothfuss | |
| 4,892,244 A | 1/1990 | Fox et al. | |
| 4,923,350 A | 5/1990 | Hinksman et al. | |
| 4,941,623 A | 7/1990 | Pruitt | |
| 4,955,959 A | 9/1990 | Tompkins et al. | |
| 4,978,049 A | 12/1990 | Green | |
| 5,031,814 A | 7/1991 | Tompkins et al. | |
| 5,065,929 A | 11/1991 | Schulze et al. | |
| 5,071,052 A | 12/1991 | Rodak et al. | |
| 5,106,008 A | 4/1992 | Tompkins et al. | |
| 5,116,349 A | 5/1992 | Aranyi | |
| 5,129,570 A | 7/1992 | Schulze et al. | |
| 5,201,746 A | 4/1993 | Shichman | |
| 5,221,036 A | 6/1993 | Takase | |
| 5,236,440 A | 8/1993 | Hlavacek | |
| 5,240,163 A | 8/1993 | Stein et al. | |
| RE34,519 E | 1/1994 | Fox et al. | |
| 5,275,323 A | 1/1994 | Schulze et al. | |
| 5,289,963 A | 3/1994 | McGarry et al. | |
| D347,474 S | 5/1994 | Olson | |
| 5,307,976 A | 5/1994 | Olson et al. | |
| 5,308,576 A | 5/1994 | Green et al. | |
| 5,326,013 A | 7/1994 | Green et al. | |
| 5,350,400 A | 9/1994 | Esposito et al. | |
| 5,360,305 A | 11/1994 | Kerrigan | |
| 5,364,001 A * | 11/1994 | Bryan | A61B 17/072 227/175.1 |
| 5,364,002 A | 11/1994 | Green et al. | |
| 5,366,479 A | 11/1994 | McGarry et al. | |
| 5,381,943 A | 1/1995 | Allen et al. | |
| 5,389,098 A | 2/1995 | Tsuruta et al. | |
| 5,395,034 A | 3/1995 | Allen et al. | |
| 5,397,046 A | 3/1995 | Savage et al. | |
| 5,413,267 A | 5/1995 | Solyntjes et al. | |
| 5,413,268 A * | 5/1995 | Green | A61B 17/07207 227/176.1 |
| 5,415,334 A | 5/1995 | Williamson, IV et al. | |
| 5,415,335 A | 5/1995 | Knodell, Jr. | |
| 5,433,721 A * | 7/1995 | Hooven | A61B 17/068 227/175.1 |
| 5,439,155 A | 8/1995 | Viola | |
| 5,439,479 A | 8/1995 | Shichman et al. | |
| 5,445,304 A | 8/1995 | Plyley et al. | |
| 5,447,265 A * | 9/1995 | Vidal | A61B 17/07207 227/176.1 |
| 5,452,836 A | 9/1995 | Huitema et al. | |
| 5,456,401 A | 10/1995 | Green et al. | |
| 5,458,279 A | 10/1995 | Plyley | |
| 5,462,215 A | 10/1995 | Viola et al. | |
| 5,464,144 A | 11/1995 | Guy et al. | |
| 5,465,895 A | 11/1995 | Knodel et al. | |
| 5,470,006 A | 11/1995 | Rodak | |
| 5,470,007 A | 11/1995 | Plyley et al. | |
| 5,470,008 A | 11/1995 | Rodak | |
| 5,470,009 A | 11/1995 | Rodak | |
| 5,472,132 A | 12/1995 | Savage et al. | |
| 5,480,089 A | 1/1996 | Blewett | |
| 5,485,952 A | 1/1996 | Fontayne | |
| 5,487,500 A | 1/1996 | Knodel et al. | |
| 5,489,058 A * | 2/1996 | Plyley | A61B 17/064 227/176.1 |
| 5,497,933 A | 3/1996 | DeFonzo et al. | |
| 5,507,426 A | 4/1996 | Young et al. | |
| 5,507,773 A | 4/1996 | Huitema et al. | |
| 5,509,596 A | 4/1996 | Green et al. | |
| 5,509,920 A | 4/1996 | Phillips et al. | |
| 5,529,235 A | 6/1996 | Boiarski et al. | |
| 5,547,117 A | 8/1996 | Hamblin et al. | |
| 5,553,765 A | 9/1996 | Knodel et al. | |
| 5,554,164 A | 9/1996 | Wilson et al. | |
| 5,558,266 A | 9/1996 | Green et al. | |
| 5,562,241 A | 10/1996 | Knodel et al. | |
| 5,562,700 A | 10/1996 | Huitema et al. | |
| 5,562,701 A | 10/1996 | Huitema et al. | |
| 5,562,702 A | 10/1996 | Huitema et al. | |
| 5,564,615 A | 10/1996 | Bishop et al. | |
| 5,571,285 A | 11/1996 | Chow et al. | |
| 5,579,978 A | 12/1996 | Green et al. | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,607,095 A | 3/1997 | Smith et al. | |
| 5,615,820 A | 4/1997 | Viola | |
| 5,626,587 A | 5/1997 | Bishop et al. | |
| 5,630,539 A | 5/1997 | Plyley et al. | |
| 5,634,584 A | 6/1997 | Okorocha et al. | |
| 5,636,779 A | 6/1997 | Palmer | |
| 5,657,921 A | 8/1997 | Young et al. | |
| 5,662,258 A | 9/1997 | Knodel et al. | |
| 5,662,662 A | 9/1997 | Bishop et al. | |
| 5,662,667 A | 9/1997 | Knodel | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,678,748 A | 10/1997 | Plyley | |
| 5,680,982 A | 10/1997 | Schulze et al. | |
| 5,680,983 A | 10/1997 | Plyley et al. | |
| 5,697,542 A * | 12/1997 | Knodel | A61B 17/07207 227/175.1 |
| 5,697,543 A | 12/1997 | Burdorff | |
| 5,704,534 A | 1/1998 | Huitema et al. | |
| 5,704,898 A | 1/1998 | Kokish | |
| 5,706,998 A | 1/1998 | Blyley et al. | |
| 5,709,334 A | 1/1998 | Sorrentino et al. | |
| 5,713,505 A | 2/1998 | Huitema | |
| 5,715,988 A | 2/1998 | Palmer | |
| 5,718,359 A | 2/1998 | Palmer et al. | |

(56) References Cited

U.S. PATENT DOCUMENTS

| | | |
|---|---|---|
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,232 B1 * | 4/2004 | Vidal ............... A61B 17/07207 227/176.1 |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 * | 11/2009 | Viola ............... A61B 17/07207 227/175.1 |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 * | 1/2010 | Ortiz ............... A61B 17/07207 227/176.1 |
| 7,654,431 B2 | 2/2010 | Hueil et al. |

(56) References Cited

U.S. PATENT DOCUMENTS

| | | |
|---|---|---|
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 * | 12/2010 | Viola ............... A61B 17/068 227/175.2 |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |

(56) References Cited

U.S. PATENT DOCUMENTS

| | | | |
|---|---|---|---|
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 * | 12/2013 | Olson .............. A61B 17/07207 |
| | | | 227/175.1 |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 * | 5/2002 | Hillstead .......... A61B 17/07207 |
| | | | 606/205 |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |

(56) References Cited

U.S. PATENT DOCUMENTS

| | | |
|---|---|---|
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Baxter, III et al. |
| 2011/0290851 A1* | 12/2011 | Shelton, IV ............ A61B 34/71 227/176.1 |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1* | 3/2013 | Swensgard ...... A61B 17/07292 227/178.1 |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1* | 9/2013 | Knodel ............ A61B 17/07207 227/180.1 |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0032781 A1 | 12/2013 | Swayze et al. |
| 2013/0327809 A1 | 12/2013 | Shelton, IV et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |

(56) References Cited

U.S. PATENT DOCUMENTS

| | | |
|---|---|---|
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0007621 A1 | 3/2015 | Shelton, IV et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

OTHER PUBLICATIONS

International Searching Authority, U.S., The International Search Report and the Written Opinion of the International Searching authority for international application PCT/US2014/027768, titled "Surgical Stapler with Expandable Jaw", dated Jul. 25, 2014.

(56) References Cited

OTHER PUBLICATIONS

The International Bureau of WIPO, International Preliminary Report on Patentability, dated Sep. 24, 2015, for International Application No. PCT/US2014/027768.
European Patent Office, Partial European Search Report for European Application No. EP 14762896.0, entitled "Surgical Stapler With Expandable Jaw," dated Apr. 10, 2017, 6 pgs.
European Patent Office, European Search Report for European Application No. 07784007.2, entitled "Surgical Stapler," dated Jun. 15, 2012, 6 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
European Patent Office, International Search Report and Written Opinion for International Application No. PCT/US2014/028211, entitled "Surgical Stapler with Partial Pockets," dated Sep. 8, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
European Patent Office, Extended European Search Report for European Application No. EP 20157713.7, entitled "Surgical Stapler with Expandable Jaw," dated May 11, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, The International Search Report and Written Opinion for International Application No. PCT/US2020/067540, dated May 3, 2021, entitled "Electrosurgical System with Tissue and Maximum Current Identification," 12 pages.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/

(56) References Cited

OTHER PUBLICATIONS 019938, entitled "Surgical Stapler Having a Two-Position Lockout Mechanism," dated Sep. 10, 2020, 10 pgs.

The International Bureau of WIPO, International Preliminary Report on Patentability, for International Application No. PCT/US2020/025496 entitled "Reload Cover for Surgical System," dated Oct. 14, 2021, 12 pgs.

European Patent Office, Extended European Search Report for European Application No. EP 21173771.3, entitled "Reload Shaft Assembly for Surgical Stapler," dated Aug. 27, 2021, 10 pgs.

* cited by examiner

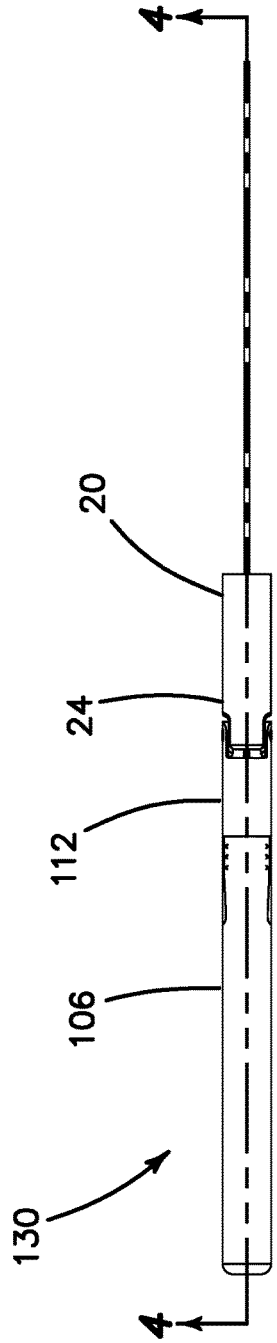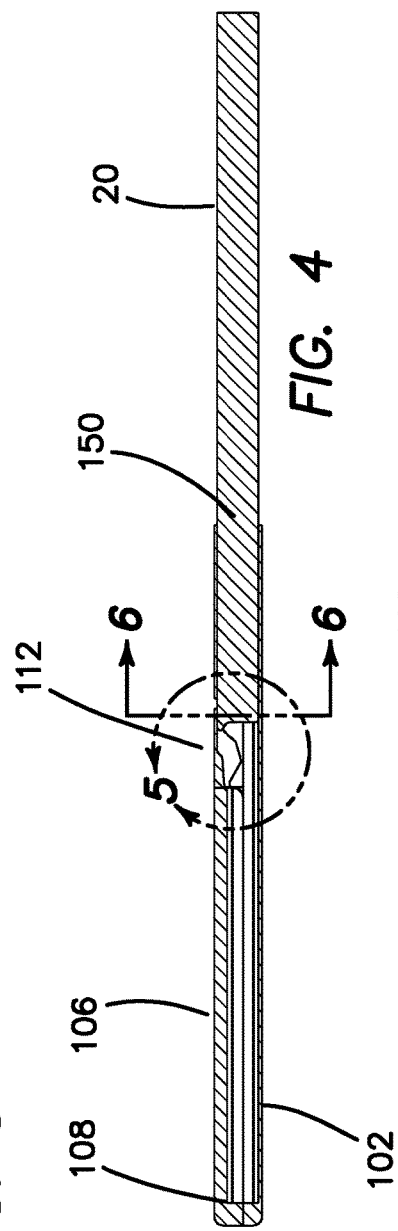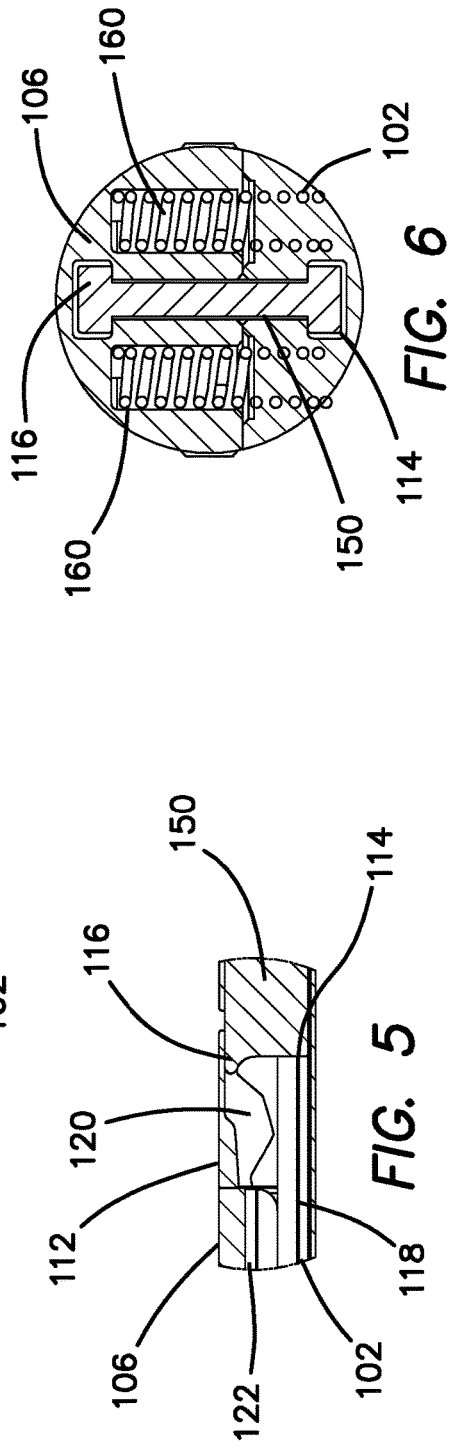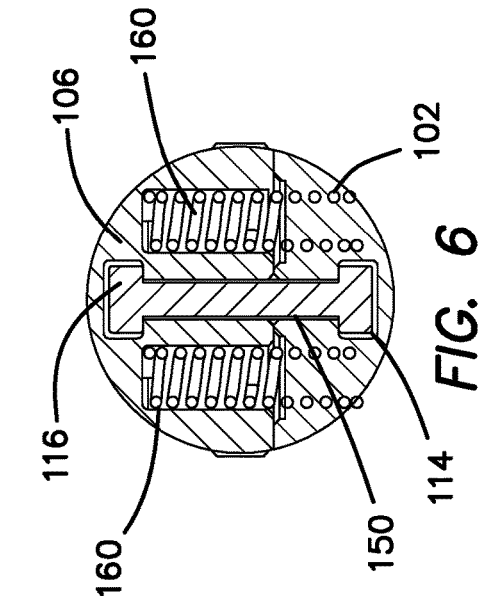

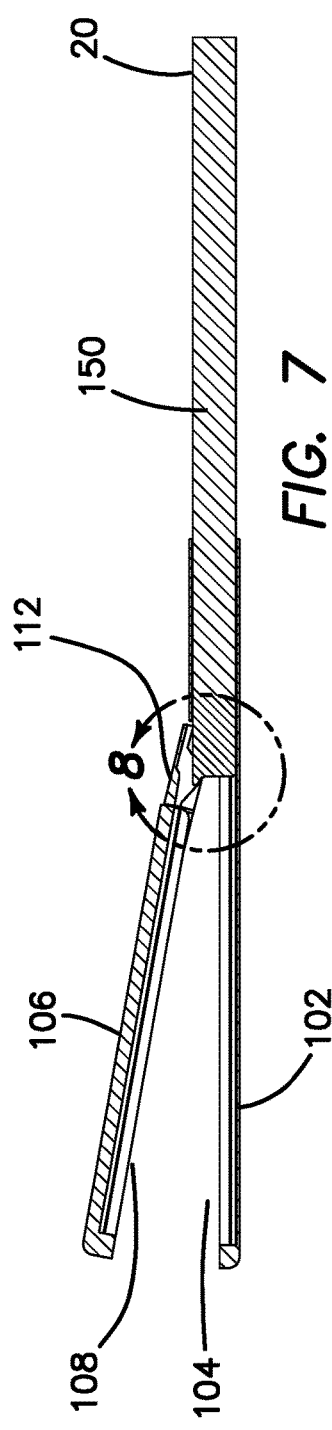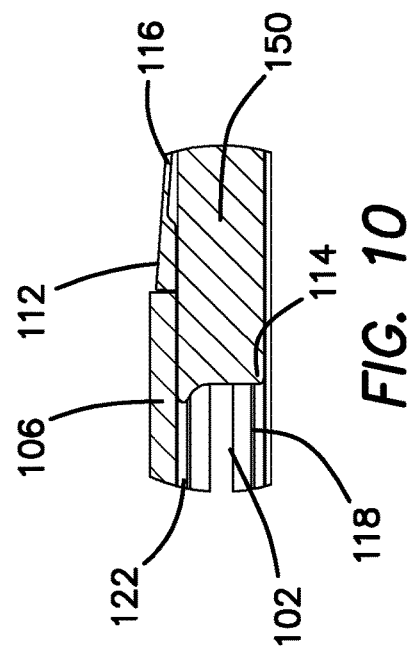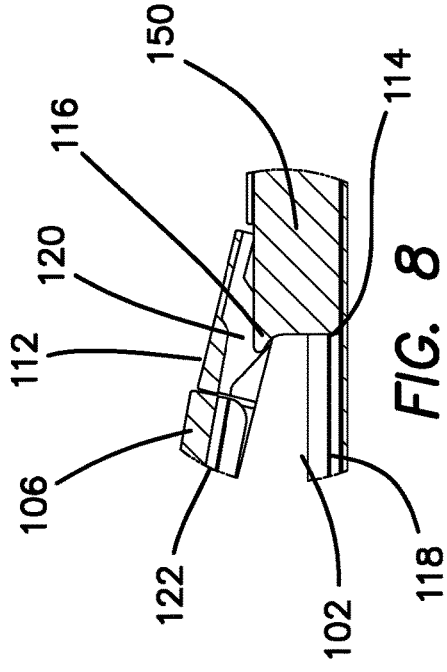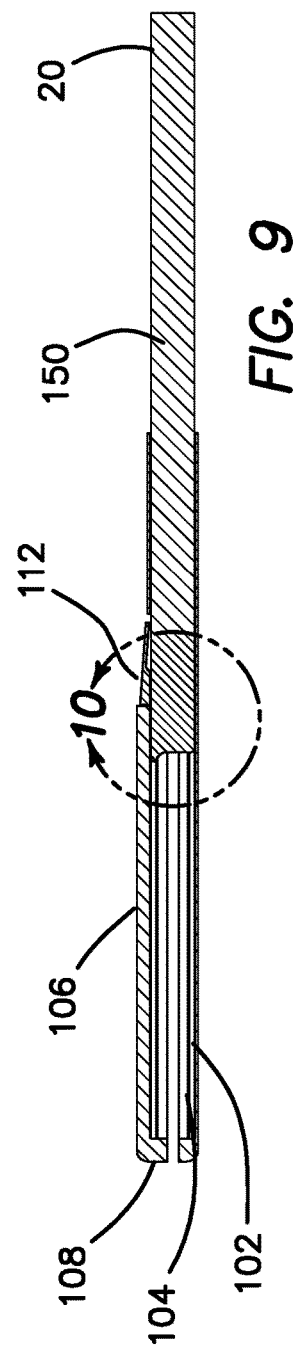

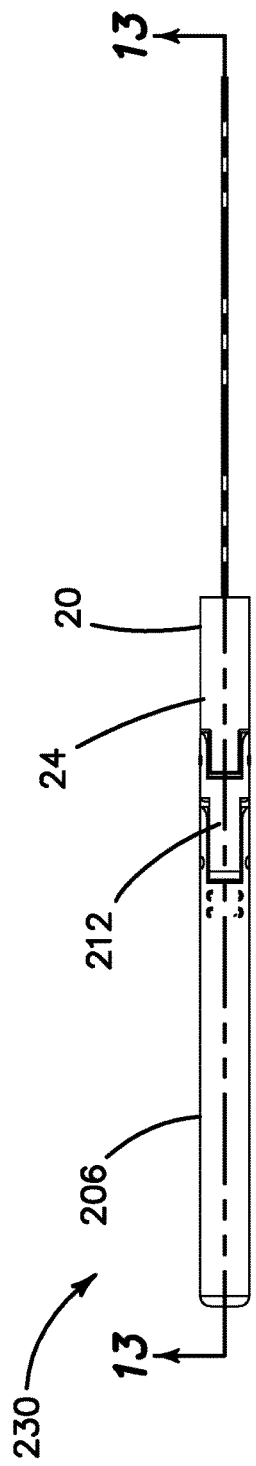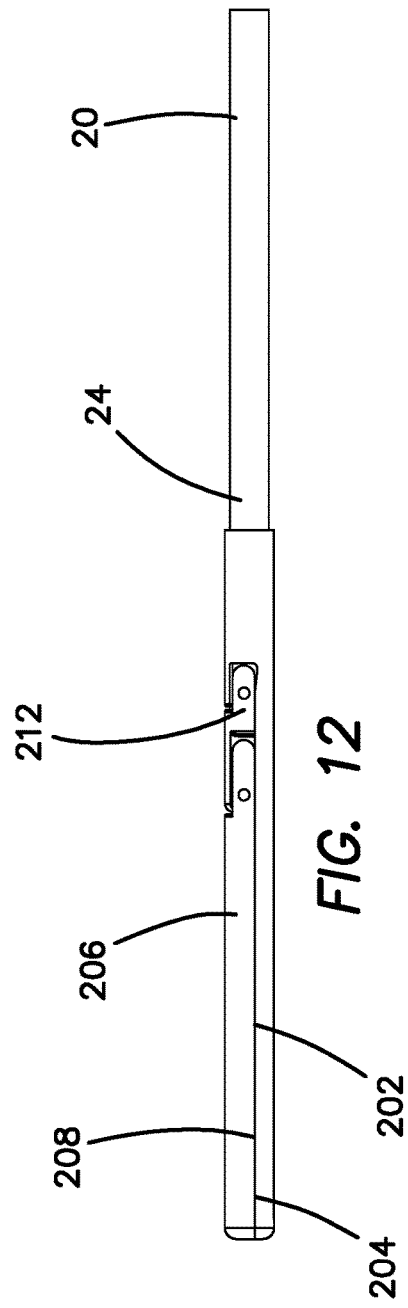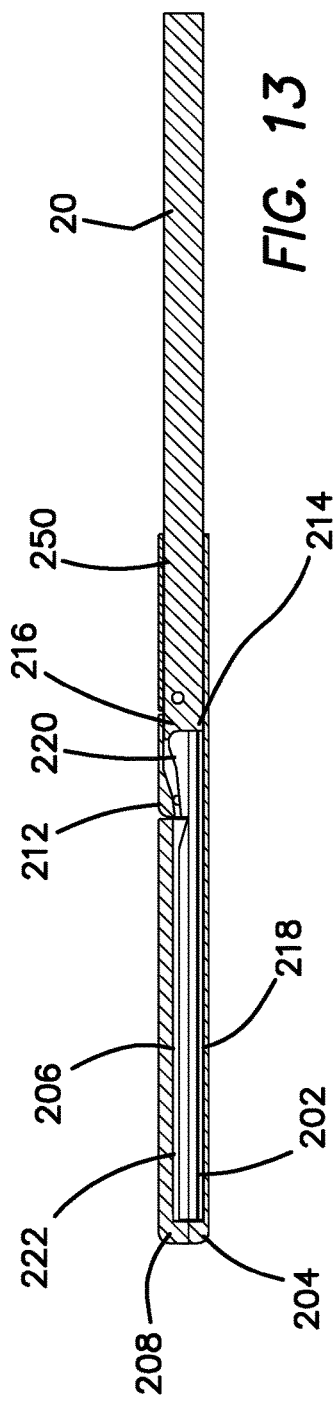

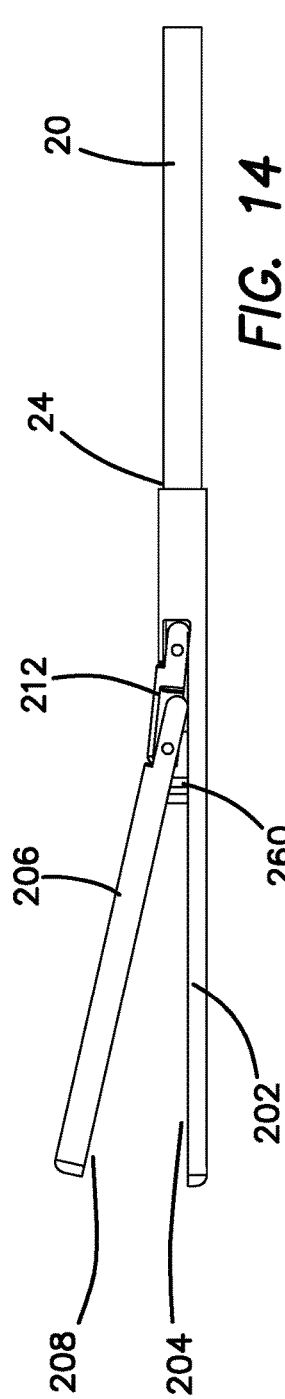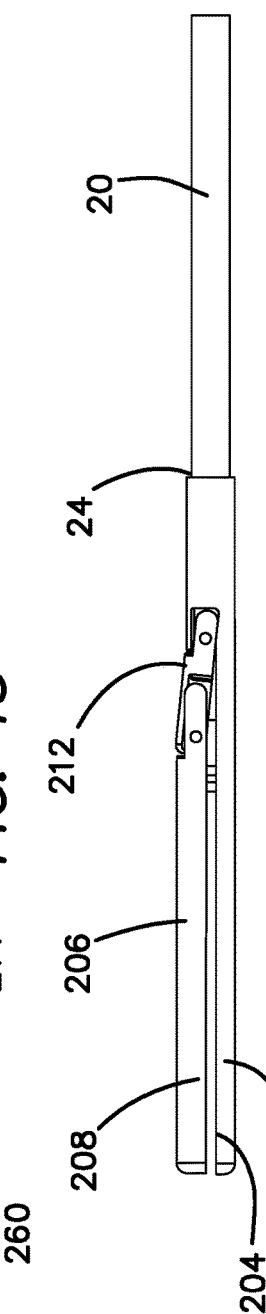
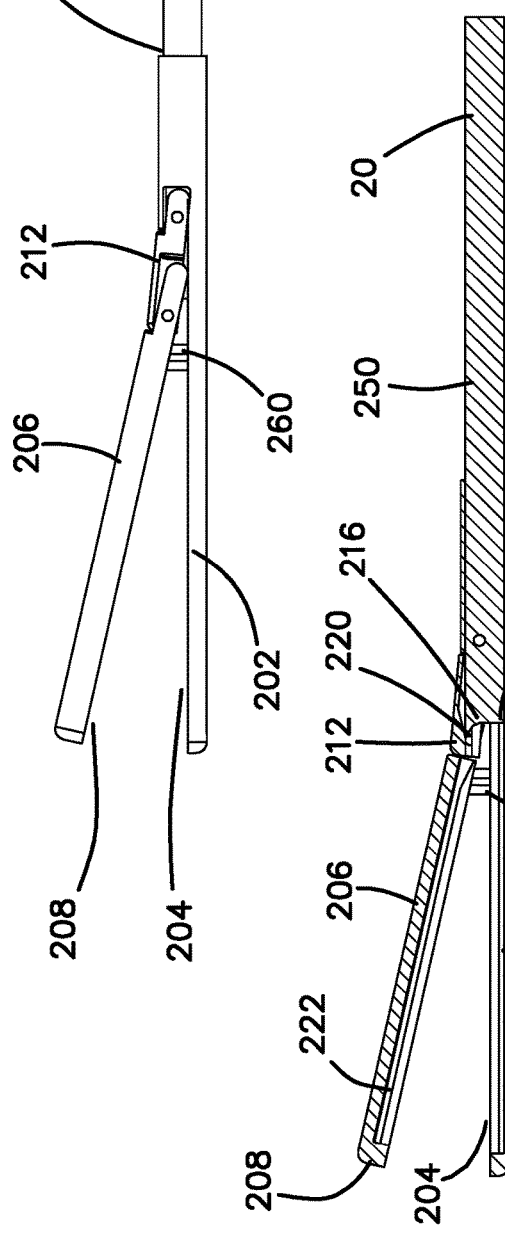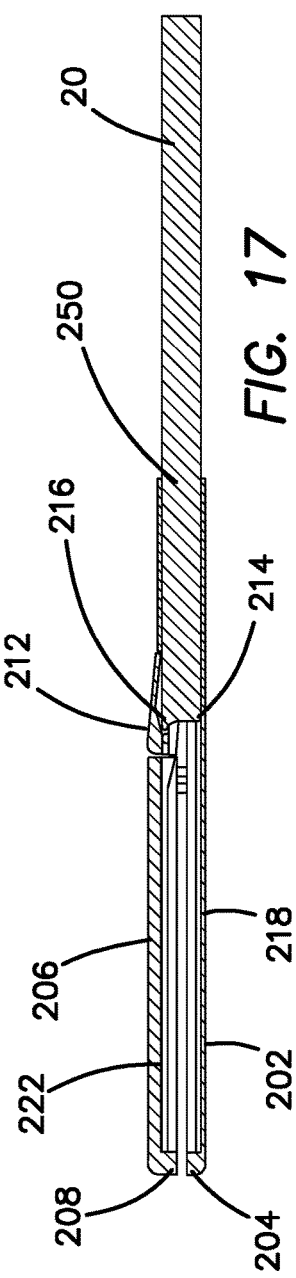

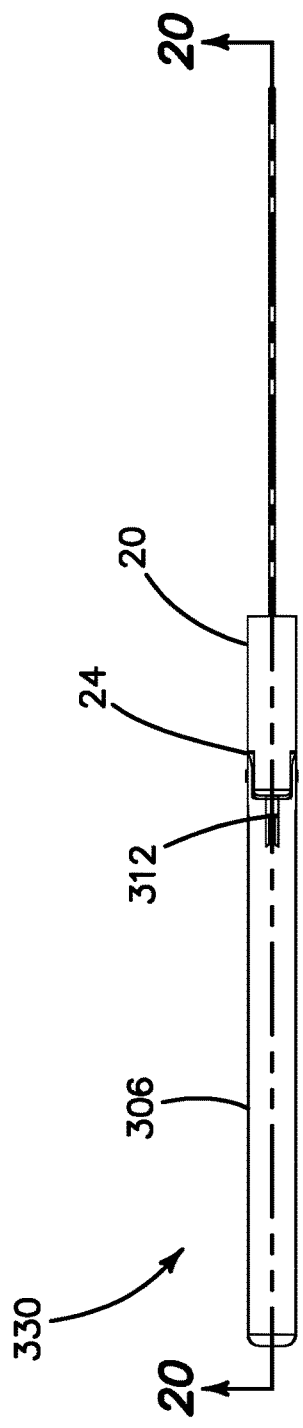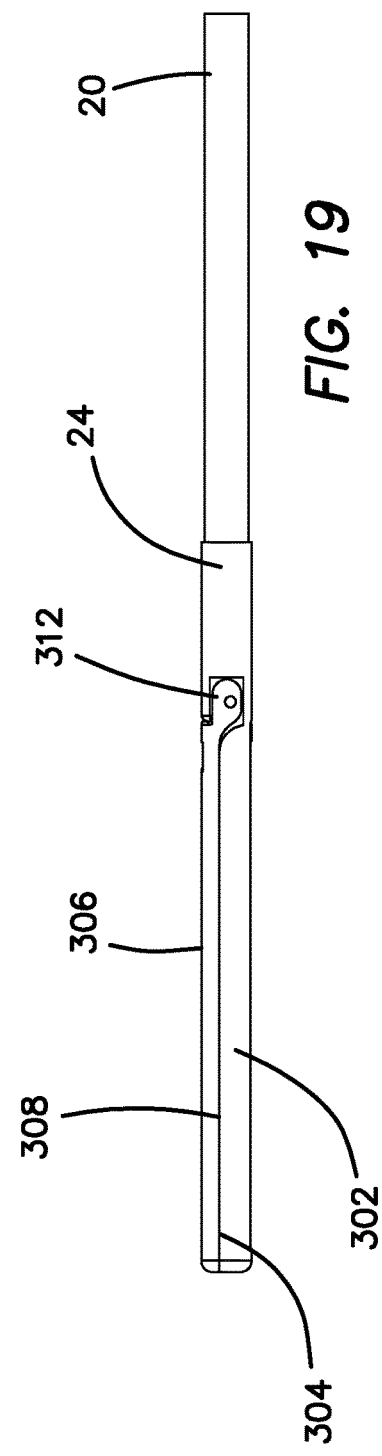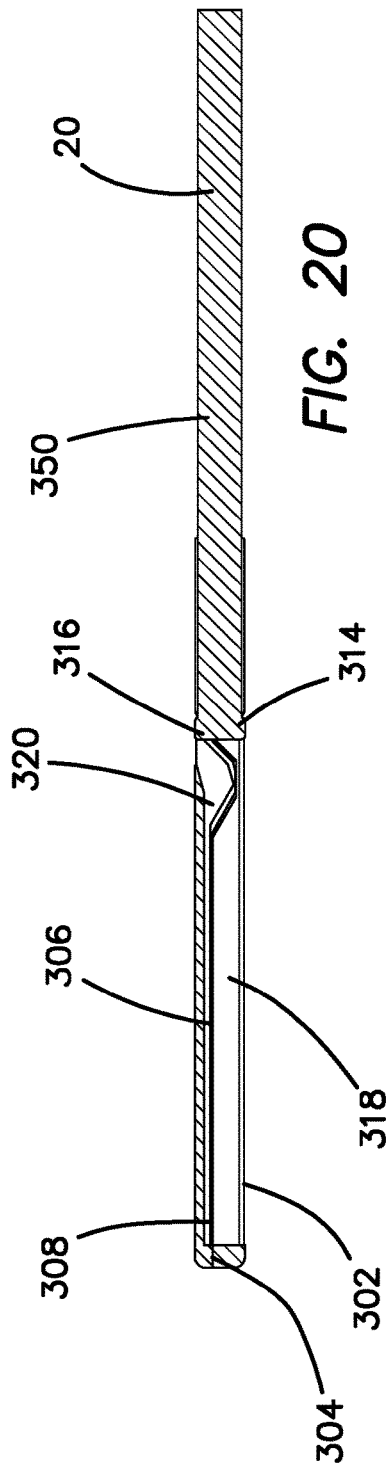

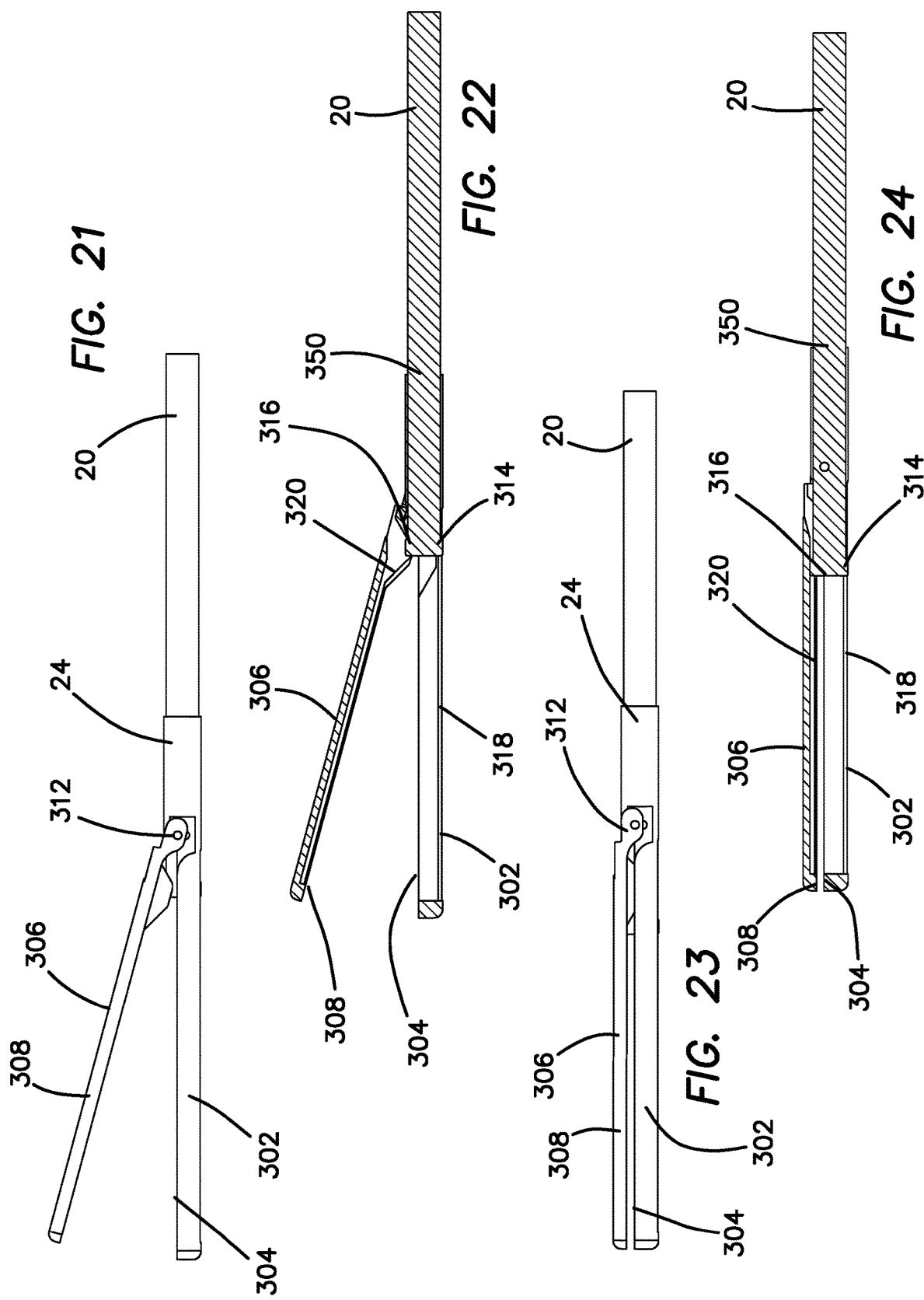

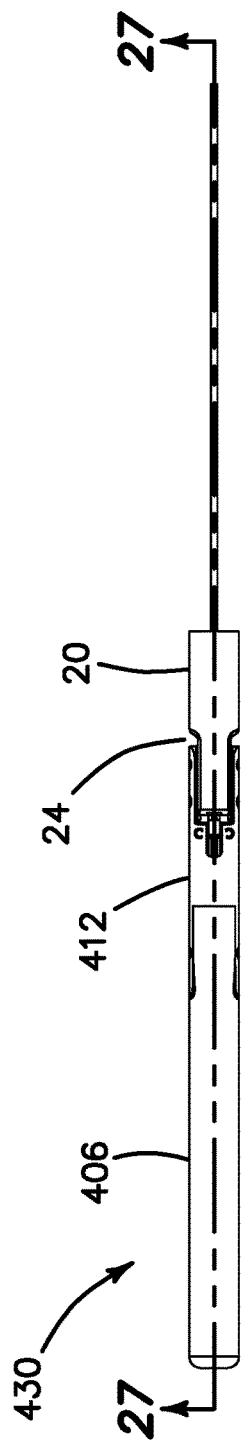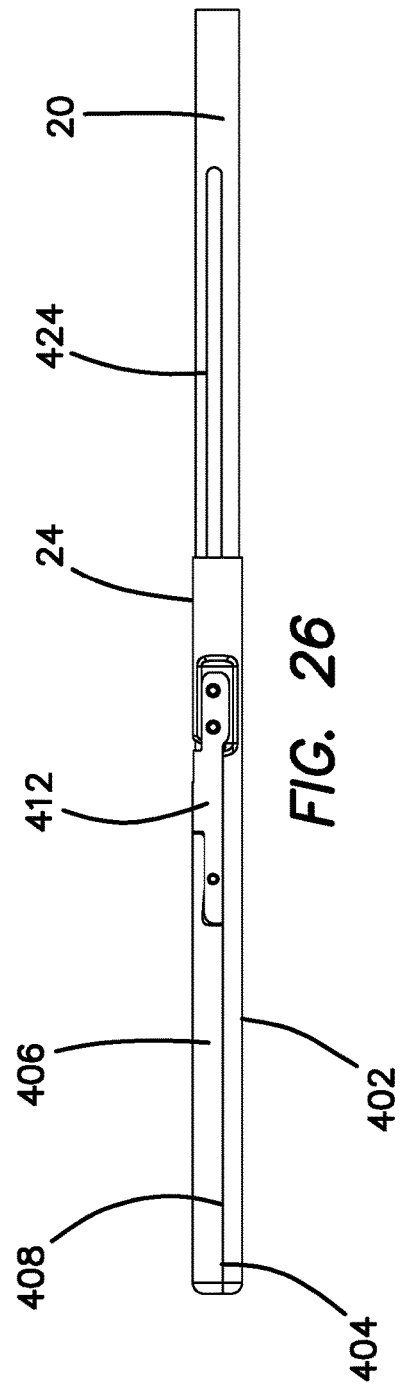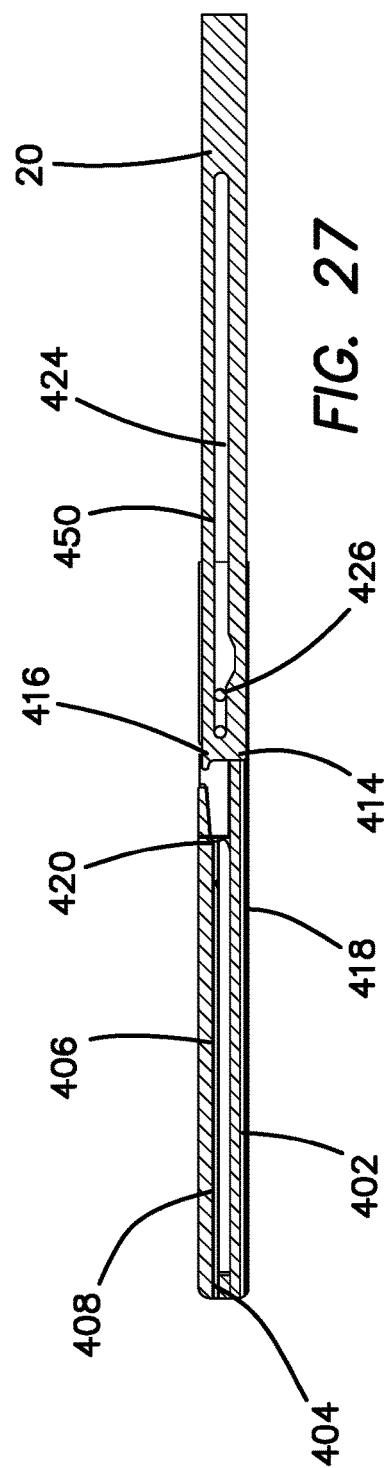

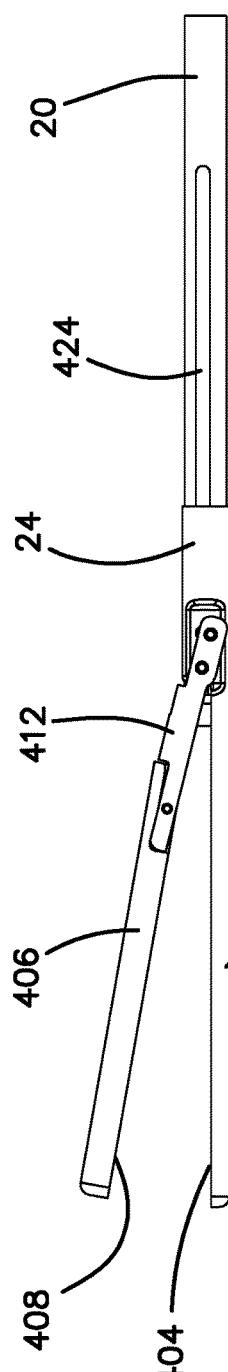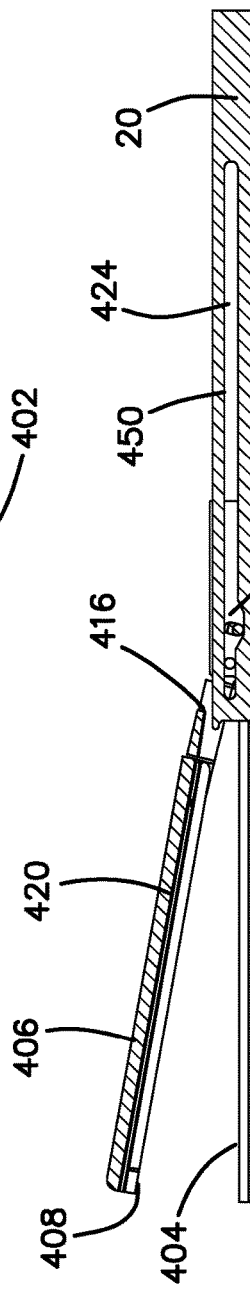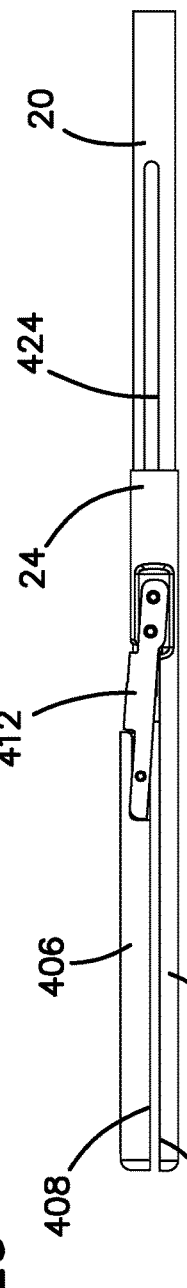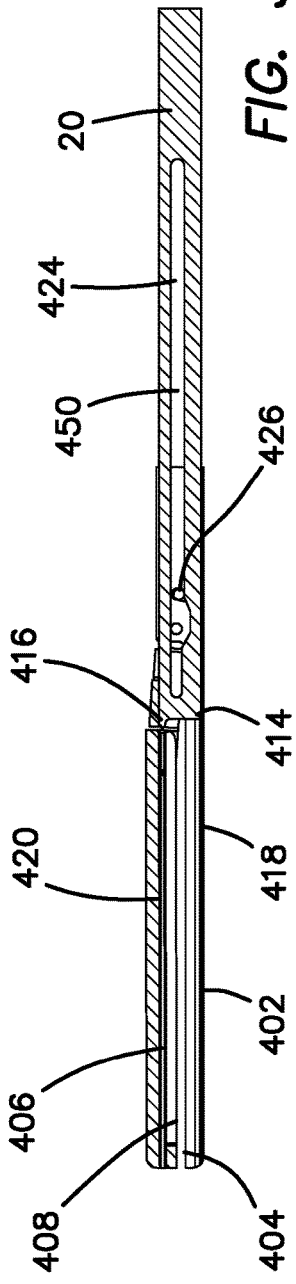

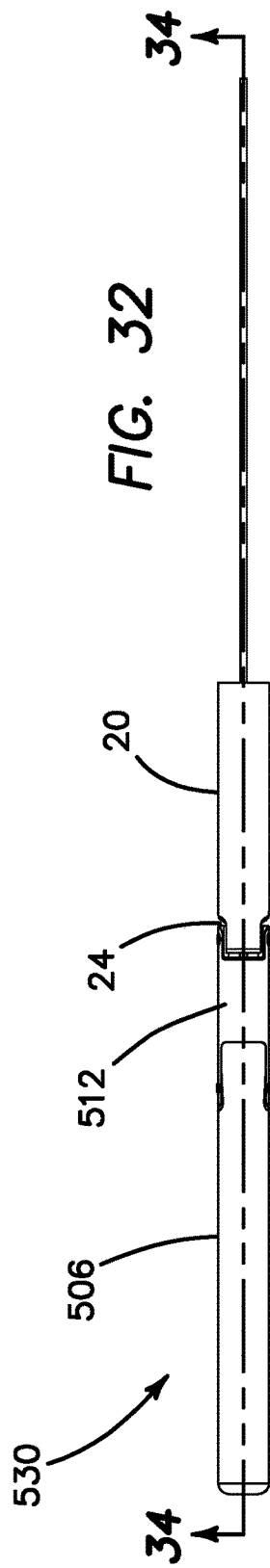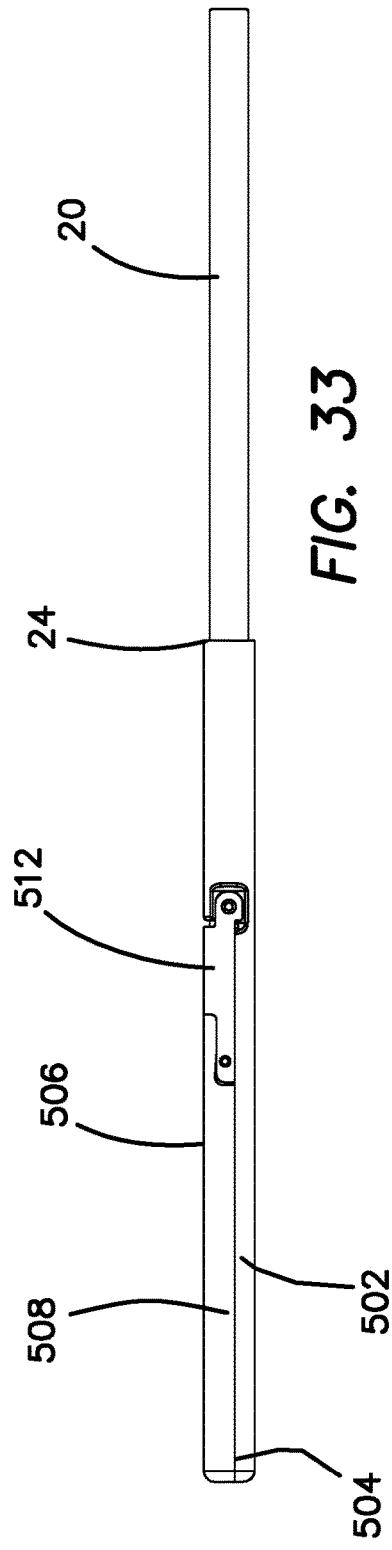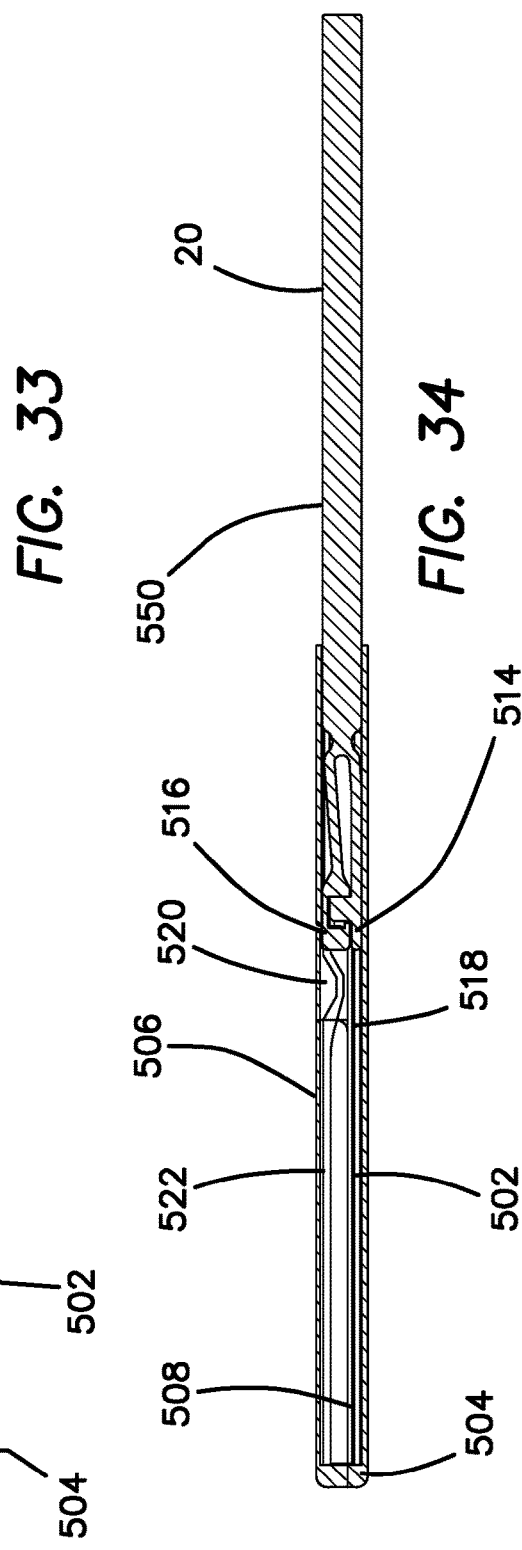

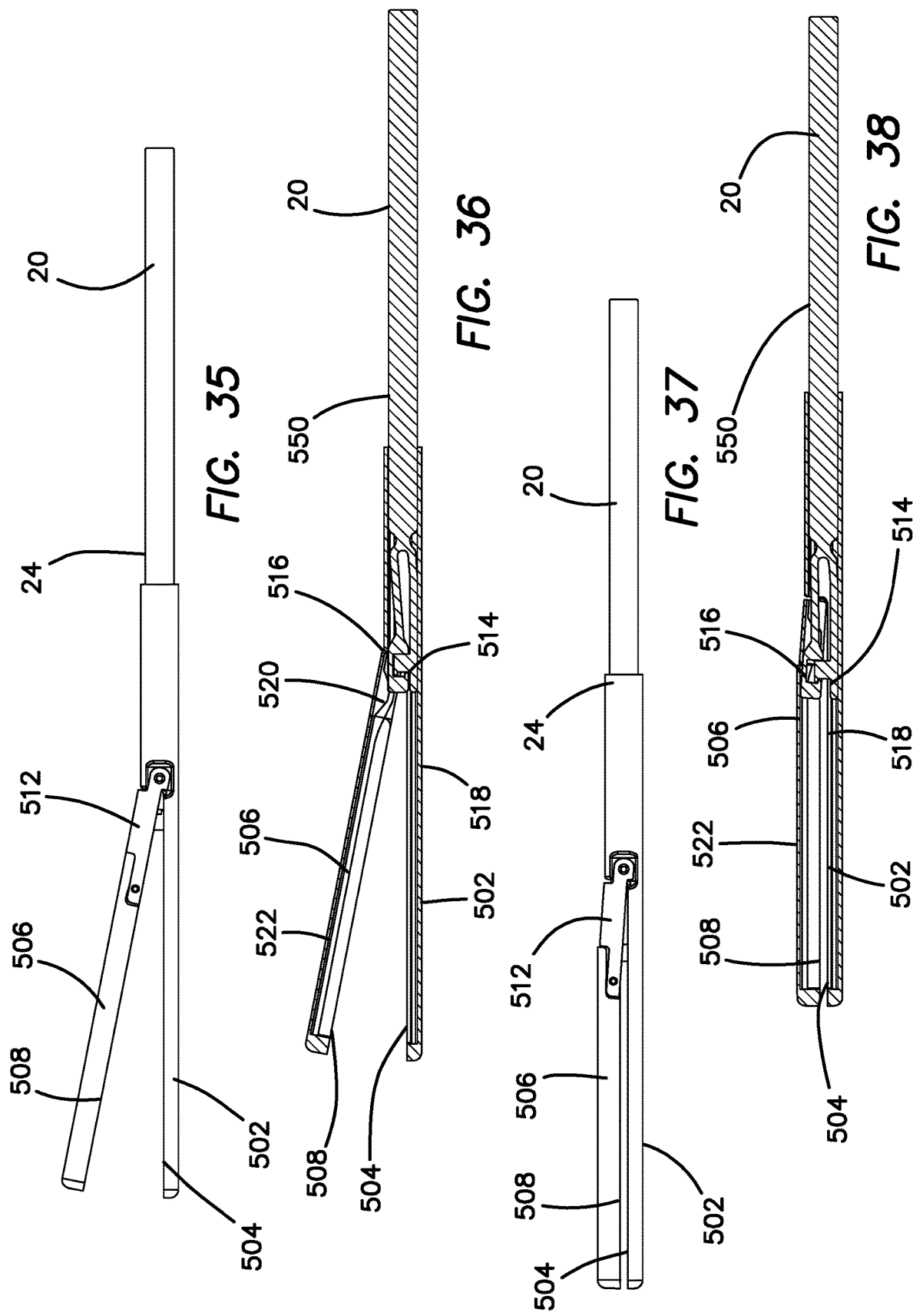

SURGICAL STAPLER WITH EXPANDABLE JAW

CROSS REFERENCE TO RELATED APPLICATIONS

This application is a continuation of U.S. patent application Ser. No. 15/788,118, entitled "SURGICAL STAPLER WITH EXPANDABLE JAW," filed Oct. 19, 2017, currently pending, which is a continuation of U.S. patent application Ser. No. 14/211,570, entitled "SURGICAL STAPLER WITH EXPANDABLE JAW," filed Mar. 14, 2014 which is now U.S. Pat. No. 9,820,742, which claims the benefit of U.S. Provisional Patent Application Ser. No. 61/793,065, entitled "SURGICAL STAPLER WITH EXPANDABLE JAW," filed on Mar. 15, 2013. The entireties of these prior applications are hereby incorporated herein by reference.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation beam extending through at least a portion of the elongate shaft. The jaw assembly is disposed at the distal end of the elongate shaft. The jaw assembly comprises a first jaw, a second jaw, and a plurality of staples positioned in the first jaw. The first jaw defines a first clamping surface. The second jaw defines a second clamping surface. The jaw assembly is actuatable by longitudinal movement of the actuation beam between a closed position in which the first clamping surface contacts the second clamping surface, an open position in which the second clamping surface extends at an angle transverse to the first clamping surface, and a stapling position in which the first clamping surface extends parallel to the second clamping surface and is spaced apart from the second clamping surface.

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation member extending through at least a portion of the elongate shaft. The actuation member comprises a first guide and a second guide thereon. The jaw assembly is disposed at the distal end of the elongate shaft. The jaw assembly comprises a first jaw, a link, and a second jaw. The first jaw extends distally from the distal end of the elongate shaft. The first jaw comprises a first guide slot extending longitudinally therein. The link has a proximal end and a distal end. The link comprises a second guide slot having a ramped opening profile formed therein. The proximal end of the link is pivotably coupled to the distal end of the elongate shaft. The second jaw extends distally from the distal end of the link. The second jaw is pivotably coupled to the distal end of the link. The second jaw comprises a third guide slot extending longitudinally therein. A plurality of staples is disposed in the first jaw. The first guide is slideable in the first guide slot and the second guide is slideable in the second guide slot and the third guide slot. Translation of the second guide distally over the ramped opening profile of the second guide slot pivots the link away from the first jaw to define an open position of the jaw assembly.

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation member extending through at least a portion of the elongate shaft. The actuation member comprises a first guide and a second guide thereon. The jaw assembly is disposed at the distal end of the elongate shaft. The jaw assembly comprises a first jaw, a second jaw, and a plurality of staples. The first jaw extends distally from the distal end of the elongate shaft. The first jaw comprises a first guide slot extending longitudinally therein and a first clamping surface. The second jaw comprises a second guide slot and a second clamping surface. The second guide slot extends in the second jaw. The second guide slot has an opening segment with a ramped profile and a stapling segment extending generally longitudinally distal of the opening segment. The second jaw is slideably coupled to the distal end of the elongate shaft such that it is movable between a closed position in which the first clamping surface contacts the second clamping surface and a stapling position in which the first clamping surface is parallel to and spaced from the second clamping surface. The second jaw is pivotably coupled to the distal end of the elongate shaft such that the first jaw is pivotable from the closed position to an open position in which the second clamping surface extends at an angle transverse to the first clamping surface. The first guide is slideable in the first guide slot and the second guide is slideable in the second guide slot such that translation of the second guide distally through the open segment of the second guide slot slides and pivots the second jaw from the closed position to the open position, and translation of the second guide distally through the stapling segment positions the second jaw in the stapling position.

BRIEF DESCRIPTION OF THE DRAWINGS

FIG. 3 is a top view of an embodiment of jaw assembly for use in a surgical stapler with the jaws in a closed configuration;

FIG. 4 is a cross-sectional side view of the jaw assembly of FIG. 3;

FIG. 5 is a detailed cross-sectional side view of the jaw assembly of FIG. 3;

FIG. 6 is a detailed cross-sectional end view of the jaw assembly of FIG. 3;

FIG. 7 is a cross-sectional side view of the jaw assembly of FIG. 3 with the jaws in an open configuration;

FIG. 8 is a detailed cross-sectional side view of the jaw assembly of FIG. 3 with the jaws in the open configuration;

FIG. 9 is a cross-sectional side view of the jaw assembly of FIG. 3 with the jaws in a firing configuration;

FIG. 10 is a detailed cross-sectional side view of the jaw assembly of FIG. 3 with the jaws in the firing configuration;

FIG. 11 is a top view of an embodiment of jaw assembly for use in a surgical stapler with the jaws in a closed configuration;

FIG. 12 is a side view of the jaw assembly of FIG. 11;

FIG. 13 is a cross-sectional side view of the jaw assembly FIG. 11;

FIG. 14 is a side view of the jaw assembly of FIG. 11 with the jaws in an open configuration;

FIG. 15 is a cross-sectional side view of the jaw assembly of FIG. 11 with the jaws in the open configuration;

FIG. 16 is a side view of the jaw assembly of FIG. 11 with the jaws in a firing configuration;

FIG. 17 is a cross-sectional side view of the jaw assembly of FIG. 11 with the jaws in a firing configuration;

FIG. 18 is a top view of an embodiment of jaw assembly for use in a surgical stapler with the jaws in a closed configuration;

FIG. 19 is a side view of the jaw assembly of FIG. 18;

FIG. 20 is a cross-sectional side view of the jaw assembly of FIG. 18;

FIG. 21 is a side view of the jaw assembly of FIG. 18 with the jaws in an open configuration;

FIG. 22 is a cross-sectional side view of the jaw assembly FIG. 18 with the jaws in the open configuration;

FIG. 23 is a side view of the jaw assembly of FIG. 18 with the jaws in a firing configuration;

FIG. 24 is a cross-sectional side view of the jaw assembly of FIG. 18 with the jaws in the firing configuration;

FIG. 25 is a top view of an embodiment of jaw assembly for use in the surgical stapler with the jaws in a closed configuration;

FIG. 26 is a side view of the jaw assembly of FIG. 25;

FIG. 27 is a side cross-sectional view of the jaw assembly of FIG. 25;

FIG. 28 is a side view of the jaw assembly of FIG. 25 with the jaws in an open configuration;

FIG. 29 is a side cross-sectional view the jaw assembly FIG. 25 with the jaws in the open configuration;

FIG. 30 is a side view of the jaw assembly of FIG. 25 with the jaws in a firing configuration;

FIG. 31 is a cross-sectional side view of the jaw assembly of FIG. 25 with the jaws in the firing configuration;

FIG. 32 is a top view of an embodiment of jaw assembly for use in a surgical stapler with jaws in a closed configuration;

FIG. 33 is a side view of the jaw assembly of FIG. 32;

FIG. 34 is a cross-sectional side view of the jaw assembly of FIG. 32;

FIG. 35 is a side view of the jaw assembly of FIG. 32 with the jaws in an open configuration;

FIG. 36 is a cross-sectional side view of the jaw assembly of FIG. 32 with the jaws in the open configuration;

FIG. 37 is a side view of the jaw assembly of FIG. 32 with the jaws in a firing configuration;

FIG. 38 is a cross-sectional side view of the jaw assembly of FIG. 32 with the jaws in the firing configuration;

DETAILED DESCRIPTION OF THE INVENTION

Figure 1:
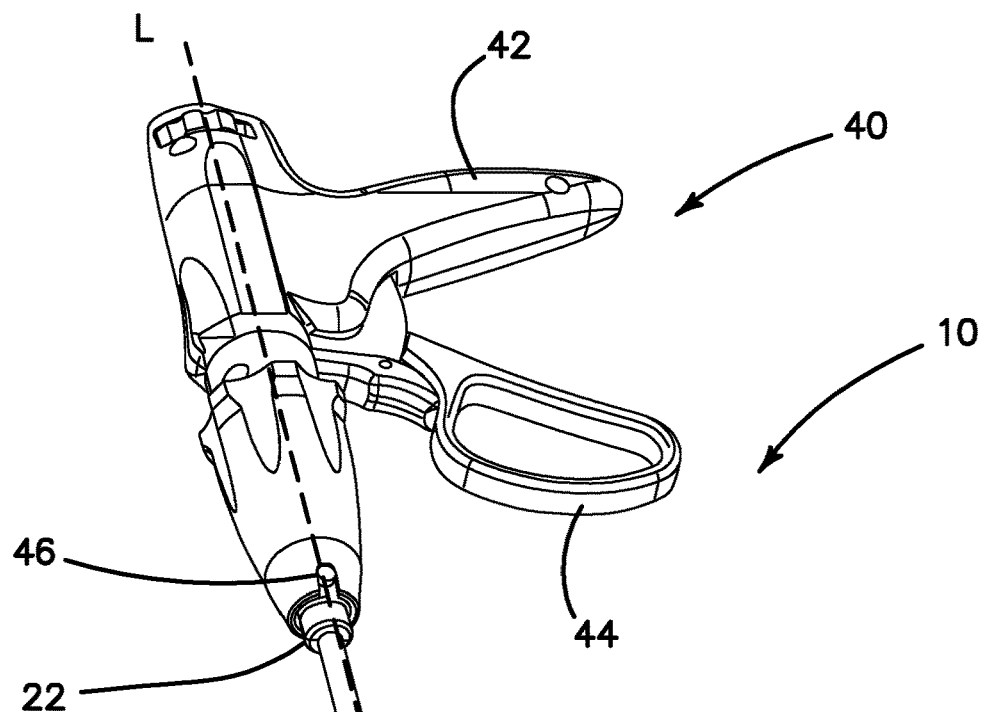
FIG. 1 is a perspective view of an embodiment of surgical stapling device with the jaws in an open configuration.
Figure 2:
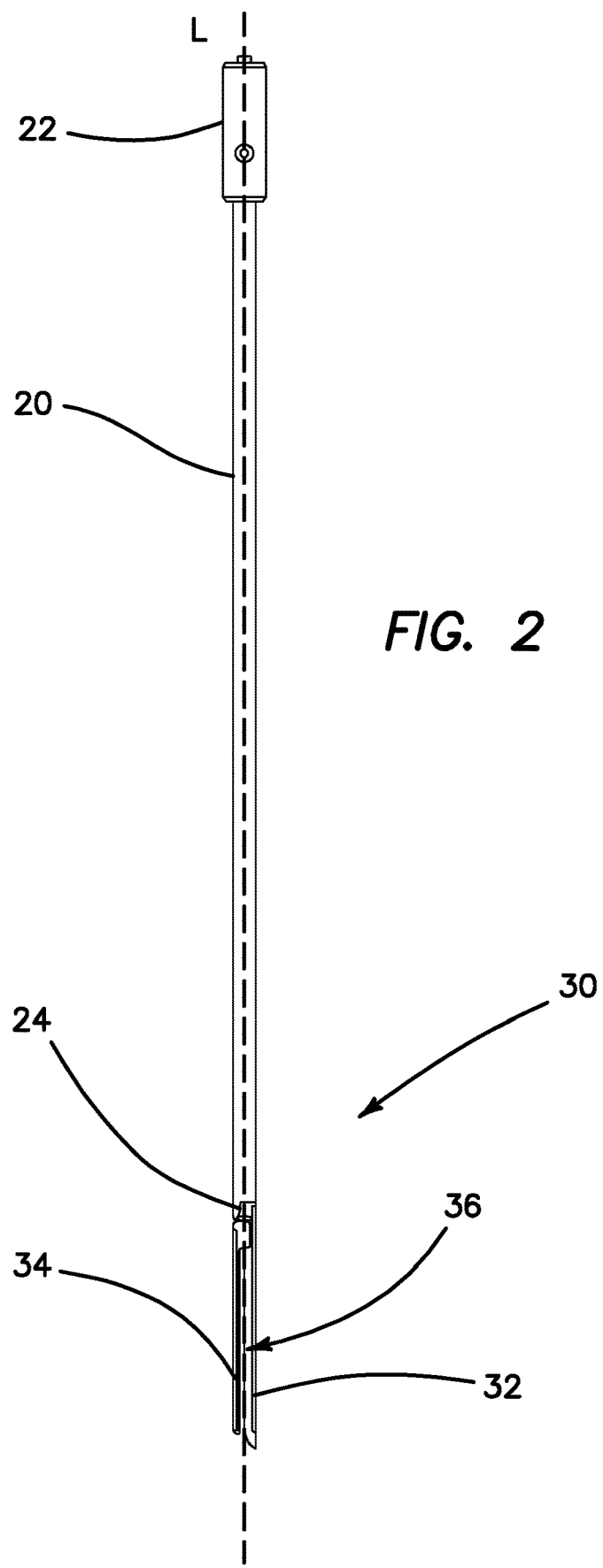
FIG. 2 is a perspective view of an embodiment of cartridge including an elongate shaft and a jaw assembly for the surgical stapling device of FIG. 1 with the jaws in a closed configuration.

With reference to FIGS. 1-2, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. FIG. 2 illustrates a removable cartridge of the surgical stapler 10 with a jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. Elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and remains stationary with respect to the elongate shaft 20. In other embodiments, it is contemplated that the jaw assembly 30 is articulable with respect to the elongate shaft 20. In an initial configuration, the first jaw 32 includes a plurality of staples 36 disposed therein. In some embodiments, staples can be initially positioned in the second jaw 34.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slideable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIGS. 1 and 2, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses an actuation mechanism configured to selectively advance an actuation shaft responsive to movement of the movable handle 44.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can a bayonet connection having an outer connector that can removably couple to handle assembly 42 the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

As discussed above, surgical staplers 10 described herein can be sized and configured for insertion into a surgical site through a relatively small diameter trocar cannula such as a so-called 5 mm trocar cannula having a working channel inner diameter smaller than about 8 mm. Desirably, jaw assemblies configured for insertion through a 5 mm trocar cannula efficiently employ the relatively limited working space to position both jaws, a plurality of staples, and staple firing elements. In a jaw assembly for a typical laparoscopic surgical stapler, with the jaw assembly in a closed or firing configuration, the first jaw is spaced apart from the second jaw by a gap to accommodate tissue clamped therebetween when the stapler is in use. However, in a jaw assembly configured for insertion through 5 mm trocar cannula, this spacing of the first jaw from the second jaw in the closed position can undesirably be wasted working space. Accordingly, it can be desirable to configure operation of a jaw assembly configured for insertion through a 5 mm trocar cannula such that the gap that would otherwise be wasted working space is repurposed to enhance stapling performance. For example, in a jaw assembly configured to eliminate the gap, the otherwise wasted working space can be repurposed to provide larger staples or more robust staple driving hardware. In various embodiments, jaw assemblies are provided herein that reduce or eliminate the gap between the first jaw and the second jaw in a closed configuration such that the working space of a relatively small diameter surgical stapler can be maximized.

With reference to FIGS. 3-10, an embodiment of jaw assembly 130 is illustrated. FIG. 3 illustrates a top view of the jaw assembly 130 with the jaws in a closed configuration, and FIGS. 4-6 illustrate cross-sectional views of the jaw assembly 130 in the closed configuration. In the illustrated embodiment, the jaw assembly 130 comprises a first jaw 102 having a first clamping surface 104, a second jaw 106 having a second clamping surface 108, and a link 112. The first jaw 102 extends distally from the distal end 24 of the elongate shaft 20 (FIGS. 1-2) and is fixed to the elongate shaft 20. The second jaw 106 is pivotably coupled to the first jaw 102. In the illustrated embodiment, the second jaw 106 is pivotably coupled to the distal end 24 of the elongate shaft 20 by the link 112. For example, the link 112 can extend from a proximal end, which is pivotably coupled to the distal end 24 of the elongate shaft 20, such as with a pinned connection to a distal end, which is pivotably coupled to the second jaw 106, such as with a pinned connection.

An actuation mechanism is operably coupled to the handle assembly 40 and actuatable by the movable trigger 44 to actuate the jaw assembly 130 in an open/closed mode, in a firing mode, and in a reverse mode. The jaws 102, 106 of the jaw assembly 130 are thus actuatable between a closed configuration in which the first clamping surface 104 of the first jaw 102 is in contact with or is immediately adjacent to the second clamping surface 108 of the second jaw 106, an open configuration in which the second clamping surface 108 extends at an angle transverse to the longitudinal axis L away from the first clamping surface 104, and a stapling or firing configuration in which the second clamping surface 108 is substantially parallel to the first clamping surface 104 and is spaced therefrom. With the jaws in the stapling or firing configuration, a plurality of staples can be deployed from the first jaw 102 through tissue positioned between the first and second jaws 102, 106 and formed against the second clamping surface 108 of the second jaw 106. In some embodiments, the actuation mechanism includes an actuation member such as an actuation beam 150 that is longitudinally slideable in the elongate shaft 20. The actuation beam 150 can include a first guide 114 and a second guide 116 formed thereon.

With reference to FIG. 6, in some embodiments, a distal end of the actuation beam 150 comprises an 'I-beam' cross sectional profile with the first and second guides 114, 116 being defined by the horizontal segments of the 'I,' and the vertical segment of the 'I' comprising the actuation beam 150. In other embodiments, the actuation member or beam can have another guide configuration. For example, the guides can comprise posts, tabs, or other projections extending from the actuation member.

With reference to FIGS. 4-5, the first jaw 102 can comprise a first guide slot 118 configured to receive the first guide 114 of the actuation beam 150 in sliding engagement. As illustrated, the first guide slot 118 can extend generally longitudinally distally from the distal end 24 of the elongate shaft 20.

With continued reference to FIGS. 4-5, in the illustrated embodiment, the link 112 can comprise a second guide slot 120 formed therein. The second guide slot 120 can extend from a proximal end to a distal end of the link 112 and can include an initial closed segment at the proximal end of the link 112, an opening segment distal the closed segment, and a firing transition segment at the distal end of the link 112.

With reference to FIGS. 4-8, the open segment has a curved or angular profile oriented such that distal sliding of the second guide 116 through the second guide slot 120 distal of the initial closed segment pivots the link 112 (and the second jaw 106 pivotably coupled thereto) away from the first jaw 102 to actuate the jaw assembly 130 from an initial closed position in which the jaw assembly has a relatively low diameter for insertion into a surgical port to an open position for receiving tissue between the first and second jaws 102, 106. In some embodiments, the link 112 can be biased away from the first jaw 102. For example, as illustrated, the jaw assembly 130 can comprise at least one spring 160 biasing the link 112 away from the first jaw 102. This bias can tend to engage the second guide 116 with the opening segment of the second guide slot 120 and position the second jaw 106 in the open position (FIGS. 7-8).

With reference to FIGS. 9-10, once tissue has been positioned between the first jaw 102 and the second jaw 106 in the open configuration at a desired stapling position, the actuation member 150 can be further advanced distally to position the jaws 102, 106 of the jaw assembly 130 in a stapling or firing configuration. Further distal movement of the actuation beam 150 advances the second guide 116 over the firing transition segment of the second guide slot 120 of the link 112 to pivot the second jaw to a position spaced apart from the first jaw a predetermined distance. The predetermined distance can be selected based on a desired tissue type for stapling in a procedure or a given staple geometry. Further distal movement of the actuation member 150 causes the second guide 116 to be received in a third guide slot 122 disposed in the second jaw 106. The third guide slot 122 can include a chamfer, radiused edge, or another transition feature to facilitate the translation of the second guide 116 distally from the second guide slot 120 to the third guide slot 122. Movement of the second guide 116 over the transition feature can further pivot the second jaw 106 such that the second clamping surface 108 is parallel to the first clamping surface 104.

As illustrated, the third guide slot 122 extends generally longitudinally along the second jaw 106 generally parallel to the second clamping surface 108 such that further distal advancement of the second guide 116 within the third guide slot 122 maintains the parallel orientation of the first and second clamping surfaces 104, 108 in the firing configuration. In other embodiments, it is contemplated that the third guide slot can extend along a curvilinear path or a path extending transversely to the second clamping surface 108 to generate a clamping force between the first and second clamping surfaces 104, 108 as the actuation member 150 is advanced distally.

With reference to FIGS. 9-10, in some embodiments, a distal end of the actuation member 150 can engage a staple driver. As the actuation member 150 is advanced distally with the jaws 102, 106 of the jaw assembly 130 in the firing position, the staple driver can deploy staples from the first jaw 102. The staple driver can include a cutting blade configured to cut tissue between rows of staples deployed by the jaw assembly.

With reference to FIGS. 11-17, another embodiment of jaw assembly 230 for use with a surgical stapler 10 is illustrated. In the illustrated embodiment, the jaw assembly 230 comprises a first jaw 202 having a first clamping surface 204 and comprising a first guide slot 218, a link 212 comprising a second guide slot 220, and a second jaw 206 having a second clamping surface 208 and comprising a third guide slot 222. An actuation member 250 or beam comprising a first guide 214 and a second guide 216 can actuate the jaw assembly 230 from the closed configuration (FIGS. 11-13), to the open configuration (FIGS. 14-15) to the firing or stapling configuration (FIGS. 16-17) in a sequence of operation substantially as described above with respect to the jaw assembly 130 of FIGS. 3-10.

With reference to FIG. 14, unlike the jaw assembly 130 of FIGS. 3-10, the second jaw 206 of the jaw assembly 230 is directly biased away from the first jaw 202. For example, in the illustrated embodiment a spring 260 is coupled to the first jaw 202 and the second jaw 206 to bias the second jaw 206 away from the first jaw. Additionally, the jaw assembly 230 includes a pivotal stop preventing excess pivoting of the second jaw 206 relative to the first jaw 202. In the illustrated embodiment, the second jaw 206 can comprise an extension such as an arm that extends proximally past the pivotal coupling of the second jaw 206 to the link 212. The extension can be sized and configured to engage the first jaw 202 when the jaw assembly 230 is positioned in the open configuration to interfere with further pivoting of the second jaw 206 away from the first jaw 202.

With reference to FIGS. 18-24, an embodiment of jaw assembly 330 for use with a surgical stapler 10 having a sliding pivot point is illustrated. In the illustrated embodiment, the jaw assembly 330 comprises a first jaw 302 having a first clamping surface 304 and comprising a first guide slot 318 and a second jaw 306 having a second clamping surface 308 and comprising a second guide slot 320. An actuation member 350 or beam comprising a first guide 314 and a second guide 316 can actuate the jaw assembly 330 from the closed configuration (FIGS. 18-20), to the open configuration (FIGS. 21-22) to the firing or stapling configuration (FIGS. 23-24) in a sequence of operation similar to those described above with respect to the jaw assemblies 130, 230.

With reference to FIGS. 20-23, in the illustrated embodiment of jaw assembly 330, the second jaw 306 is coupled to the first jaw 302 without an intercoupled link 112, 212 therebetween. Rather, the jaw assembly 330 includes a sliding pivot joint 312 that allows the second jaw 306 to pivot about a point that is translatable with respect to the first jaw 302. For example, the sliding pivot joint 312 can comprise a pivoting pin disposed in a slot formed in the first jaw 302.

With continued reference to FIGS. 20-23, the second guide slot 320 disposed in the second jaw 306 can comprise an opening segment adjacent a proximal end of the second guide slot and a firing transition segment distal the opening segment. Distal movement of the actuation member 350 distally advances the second guide 316 along the opening segment of the second guide slot 320 to slide the second jaw 306 away from the first jaw 302 and pivot the second jaw 306 into the open configuration (FIGS. 21-22). Further distal movement of the actuation member distally advances the second guide 316 past the firing transition segment and into a firing segment extending generally longitudinally along the second jaw 306 to position the jaw assembly 330 in a firing configuration (FIGS. 23-24).

With reference to FIG. 25-31, an embodiment of jaw assembly 430 with a slotted actuator for use in a surgical stapler 10 is illustrated. In the illustrated embodiment, the jaw assembly 430 comprises a first jaw 402 having a first clamping surface 404 and comprising a first guide slot 418, a link 412, and a second jaw 406 having a second clamping surface 408 and comprising a second guide slot 420. An actuation member 450 or beam comprising a first guide 414 and a second guide 416 can actuate the jaw assembly 430 from the closed configuration (FIGS. 25-27), to the open configuration (FIGS. 28-29) to the firing or stapling configuration (FIGS. 30-31) in a sequence of operation similar to those described above with respect to the jaw assemblies 130, 230.

With reference to FIGS. 27-29, the link 412 can include a third guide 426 thereon, such as one or more pins, tabs, or posts extending therefrom. The actuation member 450 can include a third guide slot 424 formed therein. The third guide 426 of the link 412 can be slideably engaged in the third guide slot 424. The third guide slot 424 can comprise an opening segment and a firing transition segment which extend transverse to the longitudinal axis. When the actuation member 450 is advanced distally from an initial position, the third guide 426 of the link 412 passes through the opening segment such that the link 412 is pivoted away from the first jaw 402 (FIGS. 28-29). Continued translation of the actuation member 450 advances the third guide 426 of the link 412 past the firing transition segment of the third guide slot 424 to position the second jaw 406 in the firing position (FIGS. 30-31).

With reference to FIGS. 32-38, another embodiment of jaw assembly 530 for use with a surgical stapler 10 is illustrated. In the illustrated embodiment, the jaw assembly 530 comprises a first jaw 502 having a first clamping surface 504 and comprising a first guide slot 518, a link 512 comprising a second guide slot 520, and a second jaw 506 having a second clamping surface 508 and comprising a third guide slot 522. An actuation member 550 or beam comprising a first guide 514 and a second guide 516 can actuate the jaw assembly 530 from the closed configuration (FIGS. 32-34), to the open configuration (FIGS. 35-36) to the firing or stapling configuration (FIGS. 37-38) in a sequence of operation similar to those described above with respect to the jaw assemblies 130, 230, 430.

With reference to FIGS. 34-36, in the illustrated embodiment, the actuation member 550 can include a first guide 514 positioned at a distal end of a first arm or extension and a second guide positioned at a distal end of a second arm or extension. The first and second arms can be flexibly coupled to one another such that a distance between the first guide 514 and the second guide 516 can be varied. The first and second arms can be biased away from one another. Advantageously, the variable spacing of the first guide 514 and second guide 516 can allow positioning of the third guide slot 522 in a position relatively close to an outer surface opposite the second clamping surface 508 of the second jaw 506. Accordingly, additional working space in the second jaw adjacent the second clamping surface can be freed by positioning the third guide slot 522 closer to the outer surface.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A surgical stapler comprising:
    an elongate shaft having a proximal end and a distal end and defining a longitudinal axis between the proximal end and the distal end;
    a handle assembly disposed at the proximal end of the elongate shaft;
    an actuation mechanism actuatable by the handle assembly, the actuation mechanism comprising an actuation member extending through at least a portion of the elongate shaft, the actuation member comprising a first guide and a second guide thereon;
    a jaw assembly disposed at the distal end of the elongate shaft, the jaw assembly comprising:
        a first jaw extending distally from the distal end of the elongate shaft, the first jaw comprising a first guide slot extending longitudinally therein and a first clamping surface;
        a second jaw comprising:
    a second guide slot extending therein, the second guide slot having an opening segment with a ramped profile and a stapling segment extending generally longitudinally distal of the opening segment; and
    a second clamping surface;
    wherein the second jaw is slideably coupled to the distal end of the elongate shaft such that it is movable between a closed position in which the first clamping surface is positioned adjacent the second clamping surface and a stapling position in which the first clamping surface is parallel to and spaced from the second clamping surface; and
    wherein the second jaw is pivotably coupled to the distal end of the elongate shaft such that the second jaw is pivotable from the closed position to an open position in which the second clamping surface extends at an angle transverse to the first clamping surface; and
    a plurality of staples;
        wherein the first guide is slideable in the first guide slot and the second guide is slideable in the second guide slot such that translation of the second guide distally through the open segment of the second guide slot slides and pivots the second jaw from the closed position to the open position, and translation of the second guide distally through the stapling segment positions the second jaw in the stapling position.

2. The surgical stapler of claim 1, wherein the plurality of staples is disposed in the first jaw.

3. The surgical stapler of claim 1, wherein the second jaw is slideably coupled to the elongate shaft such that with the second jaw in the closed position, the first clamping surface contacts the second clamping surface.

4. The surgical stapler of claim 1, wherein the second jaw is slideably coupled to the elongate shaft at a sliding pivot joint comprising a slot formed in the distal end of the elongate shaft, and the second jaw comprises a pin pivotally and translatably disposed in the slot.

5. The surgical stapler of claim 4, wherein the slot of the sliding pivot joint has a first end defining the closed position of the second jaw when the pin is disposed at the first end and a second end defining the open position and stapling position of the second jaw when the pin is disposed at the second end.

6. The surgical stapler of claim 1, wherein the actuation beam member has a distal end and wherein the distal end of the actuation beam member comprises an I-beam cross sectional profile.

7. The surgical stapler of claim 1, wherein the second jaw is coupled to the first jaw without an interconnected link.

8. The surgical stapler of claim 1, wherein the second guide slot comprises a firing transition segment between the opening segment and the stapling segment.

9. A surgical stapler comprising:
an elongate shaft having a proximal end and a distal end and defining a longitudinal axis between the proximal end and the distal end;
an actuation member extending through at least a portion of the elongate shaft, the actuation member having a distal end, the distal end comprising an I-beam cross sectional profile;
a jaw assembly disposed at the distal end of the elongate shaft, the jaw assembly comprising:
a first jaw extending distally from the distal end of the elongate shaft, the first jaw comprising a first clamping surface;
a second jaw comprising a second clamping surface; and
a plurality of staples;
wherein the second jaw is slideably coupled to the distal end of the elongate shaft such that it is movable between a closed position in which the first clamping surface is positioned adjacent the second clamping surface and a stapling position in which the first clamping surface is parallel to and spaced from the second clamping surface; and
wherein the second jaw is pivotably coupled to the distal end of the elongate shaft such that the second jaw is pivotable from the closed position to an open position in which the second clamping surface extends at an angle transverse to the first clamping surface.

10. The surgical stapler of claim 9, wherein the second jaw is slideably coupled to the elongate shaft at a sliding pivot joint comprising a slot formed in the distal end of the elongate shaft, and the second jaw comprises a pin pivotally and translatably disposed in the slot.

11. The surgical stapler of claim 10, wherein the first jaw comprises a first guide slot extending longitudinally therein, the first guide slot configured to receive a portion of the distal end of the actuation member.

12. The surgical stapler of claim 11, wherein the second jaw comprises a second guide slot therein, the second guide slot configured to receive a portion of the distal end of the actuation member.

13. The surgical stapler of claim 12, wherein the second guide slot comprises an opening segment with a ramped profile, a stapling segment extending generally longitudinally distal of the opening segment, and a firing transition segment between the opening segment and the stapling segment.

14. A surgical stapler comprising:
an elongate shaft having a proximal end and a distal end and defining a longitudinal axis between the proximal end and the distal end;
an actuation mechanism comprising an actuation beam extending through at least a portion of the elongate shaft, the actuation beam having a slot formed therein;
a jaw assembly disposed at the distal end of the elongate shaft, the jaw assembly comprising:
a first jaw;
a second jaw; and
a plurality of staples;
wherein the jaw assembly is actuatable by longitudinal movement of the actuation beam between a closed position, an open position, and a stapling position;
wherein the jaw assembly further comprises a link comprising a guide thereon, the guide of the link is slideably engaged in the guide slot to actuate the jaw assembly; and
wherein when the actuation beam is advanced distally from an initial position, the guide of the link passes through the opening segment such that the link is pivoted away from the first jaw to position the jaw assembly in the open position.

15. The surgical stapler of claim 14, wherein the guide comprises one of a pin, a tab, and a post extending from the link.

16. The surgical stapler of claim 14, wherein the slot comprises an opening segment extending transverse to the longitudinal axis and a firing transition segment extending transverse to the longitudinal axis.

17. The surgical stapler of claim 14, wherein upon continued translation of the actuation beam with the jaw assembly in the open position, the guide of the link advances past the firing transition segment of the guide slot to position the jaw assembly in the stapling position.

18. A surgical stapler comprising:
an elongate shaft having a proximal end and a distal end and defining a longitudinal axis between the proximal end and the distal end;
an actuation mechanism comprising an actuation beam extending through at least a portion of the elongate shaft, the actuation beam having a slot formed therein;
a jaw assembly disposed at the distal end of the elongate shaft, the jaw assembly comprising:
a first jaw;
a second jaw; and
a plurality of staples;
wherein the jaw assembly is actuatable by longitudinal movement of the actuation beam between a closed position, an open position, and a stapling position;
wherein the jaw assembly further comprises a link comprising a guide thereon, the guide of the link is slideably engaged in the guide slot to actuate the jaw assembly; and
wherein the link has a proximal end pivotably coupled to the distal end of the elongate shaft and a distal end pivotably coupled to the second jaw.

19. The surgical stapler of claim 18, wherein the guide comprises one of a pin, a tab, and a post extending from the link.

20. The surgical stapler of claim 18, wherein the slot comprises an opening segment extending transverse to the longitudinal axis and a firing transition segment extending transverse to the longitudinal axis.

* * * * *